US012293836B2

(12) United States Patent
LeBoeuf et al.

(10) Patent No.: US 12,293,836 B2
(45) Date of Patent: May 6, 2025

(54) SYSTEM AND METHOD FOR RAPID AND ACCURATE HISTOLOGIC ANALYSIS OF TUMOR MARGINS USING MACHINE LEARNING

(71) Applicant: Dartmouth-Hitchcock Clinic, Lebanon, NH (US)

(72) Inventors: Matthew LeBoeuf, Hanover, NH (US); Louis J. Vaickus, Etna, NH (US); Joshua J. Levy, Lebanon, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 0 days.

(21) Appl. No.: 18/520,496

(22) Filed: Nov. 27, 2023

(65) Prior Publication Data

US 2024/0170152 A1    May 23, 2024

Related U.S. Application Data

(62) Division of application No. 16/887,177, filed on May 29, 2020, now Pat. No. 11,830,621.

(51) Int. Cl.
| | |
|---|---|
| *A61B 6/58* | (2024.01) |
| *A61B 34/10* | (2016.01) |
| *G06N 3/08* | (2023.01) |
| *G06Q 20/10* | (2012.01) |
| *G06Q 30/018* | (2023.01) |

(Continued)

(52) U.S. Cl.
CPC ............ *G16H 50/20* (2018.01); *A61B 34/10* (2016.02); *G06N 3/08* (2013.01); *G06Q 20/102* (2013.01); *G06Q 30/0185* (2013.01); *G06T 7/0012* (2013.01); *G16H 10/40* (2018.01); *G16H 15/00* (2018.01); *G16H 30/40* (2018.01); *G16H 50/50* (2018.01); *G16H 50/70* (2018.01); *G16H 70/60* (2018.01); *H04L 63/08* (2013.01);
(Continued)

(58) Field of Classification Search
CPC ............................... G16H 50/20; A61B 34/10
USPC ......................................................... 382/131
See application file for complete search history.

(56) References Cited

U.S. PATENT DOCUMENTS

| | | |
|---|---|---|
| 2016/0253466 A1 | 9/2016 | Agaian |
| 2017/0161891 A1 | 6/2017 | Madabhushi |

(Continued)

FOREIGN PATENT DOCUMENTS

WO         2019055555 A1     3/2019

*Primary Examiner* — Reginald R Reyes
(74) *Attorney, Agent, or Firm* — Loginov & Associates, PLLC; William A. Loginov

(57) ABSTRACT

This invention provides a histologic system and method for rapidly and accurately assessing tumor margins for the presence or absence of tumor using machine learning algorithms. This affords a rapid and accurate histologic tumor readout and increase process efficiency and decreases the chance for human error. Advantageously and uniquely, the system and method allows for analyzing the tissue section as complete or incomplete as the first criteria to determine whether a tissue section is clear of tumor. A machine learning process receives whole slide images (WSI) of tissue and determines (a) if each image of the WSI contains complete/incomplete tissue samples and (b) if each image of the WSI contains tumorous tissue or an absence thereof. A reconstruction process generates a model of the tissue that maps types of tissue therein, and a display process provides results of the model or report for use and manipulation by a user.

20 Claims, 10 Drawing Sheets

(51) Int. Cl.
  *G06T 7/00* (2017.01)
  *G16H 10/40* (2018.01)
  *G16H 15/00* (2018.01)
  *G16H 30/40* (2018.01)
  *G16H 50/20* (2018.01)
  *G16H 50/50* (2018.01)
  *G16H 50/70* (2018.01)
  *G16H 70/60* (2018.01)
  *H04L 9/40* (2022.01)

(52) U.S. Cl.
  CPC ............... *G06T 2207/20081* (2013.01); *G06T 2207/30024* (2013.01); *G06T 2207/30096* (2013.01)

(56) References Cited

U.S. PATENT DOCUMENTS

| | | | |
|---|---|---|---|
| 2018/0322806 A1* | 11/2018 | Avisar | A61B 17/1227 |
| 2019/0087954 A1 | 3/2019 | Lloyd | |
| 2019/0156159 A1 | 5/2019 | Kopparapu | |
| 2021/0209753 A1* | 7/2021 | Dogdas | G06V 20/698 |
| 2021/0373024 A1* | 12/2021 | Shanmugam | G01N 33/57419 |

* cited by examiner

SYSTEM AND METHOD FOR RAPID AND ACCURATE HISTOLOGIC ANALYSIS OF TUMOR MARGINS USING MACHINE LEARNING

RELATED APPLICATION

This application is a divisional of U.S. patent application Ser. No. 16/887,177, entitled SYSTEM AND METHOD FOR RAPID AND ACCURATE HISTOLOGIC ANALYSIS OF TUMOR MARGINS USING MACHINE LEARNING, filed May 25, 2020, the teachings of which are expressly incorporated herein by reference.

FIELD OF THE INVENTION

This invention relates to systems and method for analyzing images of tissue samples for medical and research purposes, and more particularly to those employing machine learning and/or neural networks operating on computing systems

BACKGROUND OF THE INVENTION

Successful treatment of solid cancers relies on complete surgical excision of the tumor for either definitive treatment or prior to adjuvant therapy. Incomplete excision of tumors results in both local tumor recurrence and increased risk of distant metastasis and decreased survival. Recurrence rate of tumors following surgical excision range from as high as 50% for subtypes of brain cancer to as low as 0.5% for skin cancers. Tissue preparation/grossing, inking, grossing, and analysis may contribute to this wide range in local recurrence rates. Varied methodologies can be used to gross and ink the tissue prior to tissue sectioning and then analysis by the pathologist. The "breadloafing" methodology is the most commonly used technique for grossing tissue, but in its standard use, only analyzes approximately 1% of tissue margins with this number decreasing as the size of tissue increases. An advantage of the standard breadloafing methodology is that it is quick and does not require the pathologist to analyze a large amount of tissue. A less common methodology entails the use of en face margins or Mohs Micrographic Surgery, in which 100% of the peripheral and deep margin is analyzed. A caveat to en face margins is that the peripheral margins are separated from the deep margin resulting in the potential for lost information at this point. Mohs Micrographic Surgery (MMS) places relaxing cuts into the tissue allowing the peripheral margins to fall into the same plane as the deep margin allowing true 100% margin analysis without separation of the peripheral and deep margin. MMS works with fresh tissue that is rapidly frozen and sectioned resulting in tissue being ready for histologic analysis in approximately twenty minutes. Both en face margins and MMS result in very low local recurrence rates while also limiting the amount of healthy surrounding tissue removed. In cases of skin cancer, use of the above procedures, in critical anatomic areas, maintains function and facilitates reconstruction that restores normal human appearance. Note that the use of the breadloafing technique in its current form, and permanent section histology, results in taking significantly larger margins to increase the likelihood of complete tumor resection as it is not performed in real-time. Increasing the number of pieces generated and sectioned in a breadloafed model can increase the percentage of margin analyzed though this is time consuming both at the generation step and the pathologic reading step. Breadloafed sections do not have to be limited to paraffin embedded sections but could also be done using frozen tissue in order to allow it to happen in real-time.

Challenges in en face and MMS margin analysis because of the reliance upon the requirement of complete tissue sections without missing peripheral or deep margins. Complete tissue sections are critical, as holes in the tissue may have resulted from tumor "falling out" of the tissue during tissue processing. Acquiring complete tissue sections can be challenging depending on the type and size of the tissue. Therefore, during histologic analysis of the tissue, in addition to the presence or absence of tumor at the margins, the pathologist must also evaluate the tissue to ensure that it is complete. This issue also arises in the sectioning of permanent paraffin sections, but less frequently. Challenges with en face margin and MMS margin analysis is that, as the size of the tissue increases, the surface area or total margin to be analyzed increases exponentially. The time of tissue section analysis by the pathologist is directly related to the size of the tissue section on the slide and the number of slides to be analyzed which are both related to the size of the tissue specimen. Furthermore, it is not uncommon in en face or MMS margin analysis that the positive margin consists of less than 1% of the total tissue margin. This places significant stress on the pathologist to scrutinize the margin to ensure that it is adequately analyzed to prevent missed tumor. During removal of the tissue, both the remaining defect and tissue removed is oriented and tagged to ensure accurate identification of positive margins for subsequent tissue resection. Histologic analysis of the tumor results in a tissue "map" in which the presence of tumor is noted (annotated) on the tumor map. Depending on the size of section analyzed and the number of tissue sections this can be challenging to accurately and efficiently map the tumor. Subsequent resection is reliant on precise mapping and failure to accurately map the tissue results in "clear" tumor margins when, in reality, it is an incomplete tumor resection. Finally, the information must be communicated to the operating room, informing the surgeon of the location of the remaining tumor. Currently, in the operating room this is done by telephone, and in MMS a physical paper copy of the map is carried back to the operating room. Communication via telephone requires staff or the surgeon to recreate the tumor map either mentally or physically presenting the opportunity for mistakes. Alternatively, if tissue is being processed from a standard excision with post-operative margin analysis, the information must be communicated to the surgeon via pathology report.

Tissue processing, staining, histologic analysis, and tumor mapping all require time. In use cases of MMS, local anesthesia is used and the patient is placed in a nearby waiting room. In cases of tumor resection in the operating room, the patient is under general anesthesia. Not surprisingly, the risk of adverse events increases the longer a patient is under general anesthesia. Design of efficient and accurate systems aimed at decreasing tissue analysis and processing time, and increasing the speed at which information is communicated to the operating room, are highly desirable, and should desirably allow en face/MMS margin analysis or increased numbers of breadloafed sections to be performed in any setting-thereby resulting in lower recurrence rates, less tissue resection, and increased efficiency and cost-effectiveness of care. Additionally, decreasing the time required by the pathologist to read permanent sections from a standard excision will allow the pathologist to spend time in other areas of their practice or allow them to read more specimens on a daily basis.

In addition to clinical medicine, there is also an unmet need in basic, translational, and clinical research for efficient and accurate mechanisms of tumor margin analysis. Understanding the efficacy of a specific medical or surgical treatment in both animal models and early human studies rely on effectively evaluating tissue for the presence or absence of tumor. As stated above analysis of more tissue requires more time and resources which can be greatly decreased by the use of machine learning to facilitate this process. This may allow increased numbers of samples to be analyzed thereby increasing the power of the study. Just as importantly, in research settings analysis of tumor margins may be performed by individuals including students who are not experts in the field. Access to a machine learning algorithm developed and trained with whole slide images annotated by board certified and expert pathologists will aid in accurate analysis of tumor margins thereby increasing the validity of animal and human early stage studies.

SUMMARY OF THE INVENTION

This invention overcomes disadvantages of the prior art by providing a system and method for rapidly and accurately assessing histologic tumor margins for the presence or absence of tumor using machine learning algorithms that can be used in either clinical or research settings. If a tumor is present then the system and method allows for precise tumor mapping and aids the surgeon in planning for subsequent rounds of tissue resection either in real-time or a staged setting. The ability to automate the above process and provide a rapid and accurate tumor readout increases process efficiency and improves patient outcomes. Advantageously and uniquely, the system and method allows for analyzing the section as complete or incomplete as the first criteria to determine whether a tissue section is clear of tumor.

In an illustrative embodiment a system and method for generating a model of tissue for use in diagnostic and surgical procedures in clinical and research settings is provided. The system and method includes a machine learning process that receives whole slide images (WSI) of tissue removed from a patient or research (e.g.) animal model, and that determines (a) if each image of the WSI contain complete or incomplete tissue samples and (b) if each image of the WSI contain tumorous tissue or an absence of tumorous tissue. A reconstruction process generates a model of the tissue removed from the patient with a mapping of types of tissue therein, and a display process provides results of the model for use and manipulation by a user and/or a pathology report that can be adapted for uploading to an interested party. Illustratively, the machine learning process is trained using a plurality of training slide images having a plurality of differing tissue types and arrangements. The training slide images can be provided via at least one of a library of preexisting images of tissue from third parties and preexisting images generated and stored by the user. The system and method can further include a background removal process and a connected component process that pre-processes each of the slide images prior to performing the machine learning process. The model can define differing sections of the tissue based upon each of the slide images and components of the tissue within each of the sections, and/or include an infographic that is arranged to allow the user to access further information or images with respect to the sections or the components of the tissue via a user interface. Illustratively, the infographic is arranged to display a plurality of colors or other graphical representation that correspond to different types of tissue. Additionally, the machine learning process can reside, at least in part, on a remote server accessed by the user via a network. As such, an access control process can be used to authenticate the user relative to the remote server and a billing process can generate financial transactions between the user and an operator of the system with respect to operation of the system. In various embodiments, a whole slide imager is arranged to read each WSI prepared by the user and provide the slide images therefrom to the machine learning process. The slides associated with the WSI can be prepared using frozen sections or paraffin embedded sections of the tissue. Additionally, the tissue can be sectioned using an MMS, en face or breadloaf (radial) technique. In general, the pathology report can include a readout that is adapted to be uploaded to a chart of the patient.

In an illustrative embodiment, a medical treatment method performing the aforementioned system and method can be employed in whole or in part by a user. Such treatment method can be performed entirely by a single user or distributed amongst a plurality of entities or individuals.

BRIEF DESCRIPTION OF THE DRAWINGS

The invention description below refers to the accompanying drawings, of which.

DETAILED DESCRIPTION

I. Background Considerations

Figure 1:
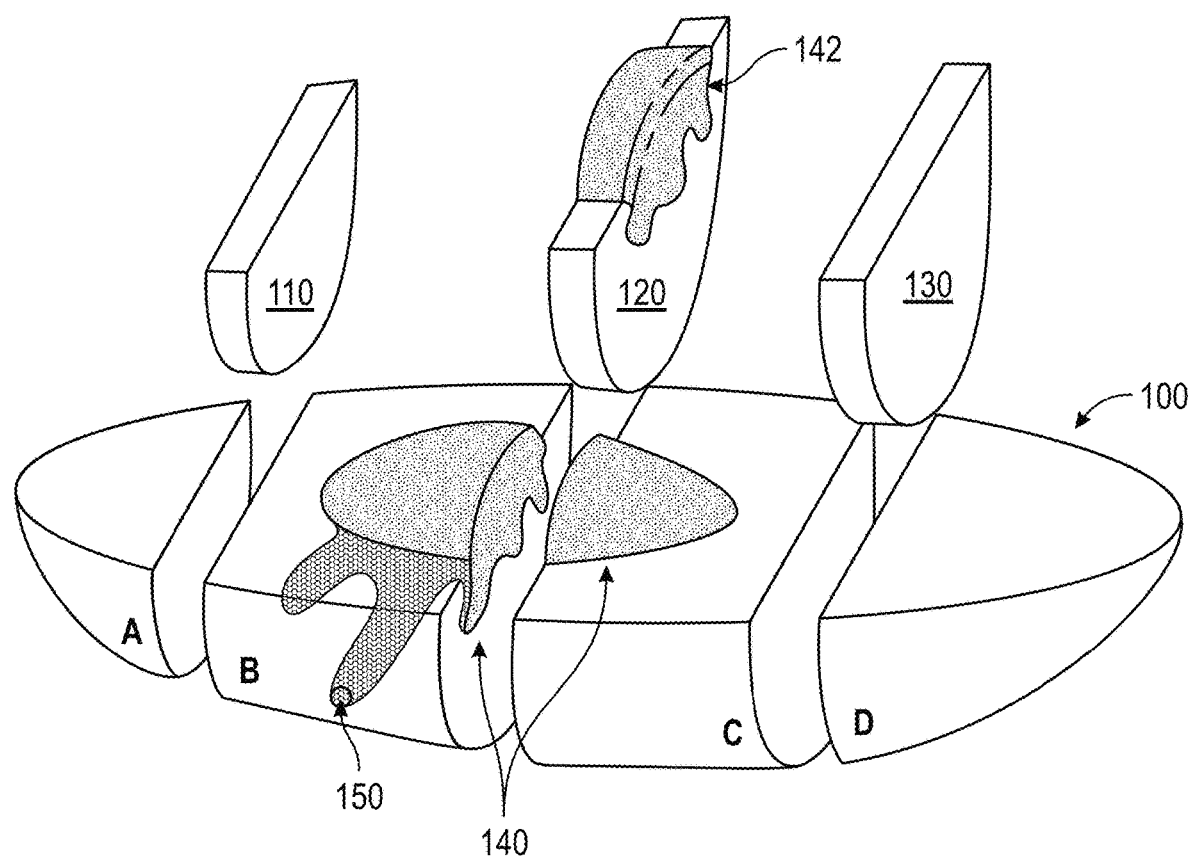
FIG. 1 is a diagram of an exemplary breadloafing process for cutting tissue slices from excised tissue, for use in creating slides that can be imaged in accordance with the system and method herein.

FIG. 1 shows a generalized diagram of an exemplary excised tumor tissue sample 100—for example a skin lesion—that has been subjected to the breadloafing technique, by way of non-limiting example. In this technique, the excised tissue sample 100 is sliced laterally, as shown, into sections (A-D), from which are taken thin slices 110, 120 and 130 at various points along the length of the tissue sample 100. The distribution of slices 100-130 through the tissue is chosen to intercept the likely extent of the cancerous growth 140 therein. Hence in slice 120, there resides a piece 142 of the overall cancerous growth 140. Based upon one or more slides (described below) that are created from the slices, the pathologist should be able to determine the boundaries of the cancerous tissue, thereby ensuring that it is completely removed by the excision process.

However, using conventional techniques, it is possible that irregularly or unpredictably shaped tumor boundaries may be overlooked by the procedure—as indicated by the missed cancer tissue 150 on the edge of the section B. As described above, this is an undesirable outcome that can result in recurrence and/or spread of the cancer. The following description can apply to the (a) MMS (b) en face, (c) breadloafed tissue sections generated from both clinical and research settings, and/or other applicable techniques that exist or can be developed by those of skill in the art.

Figure 1B:
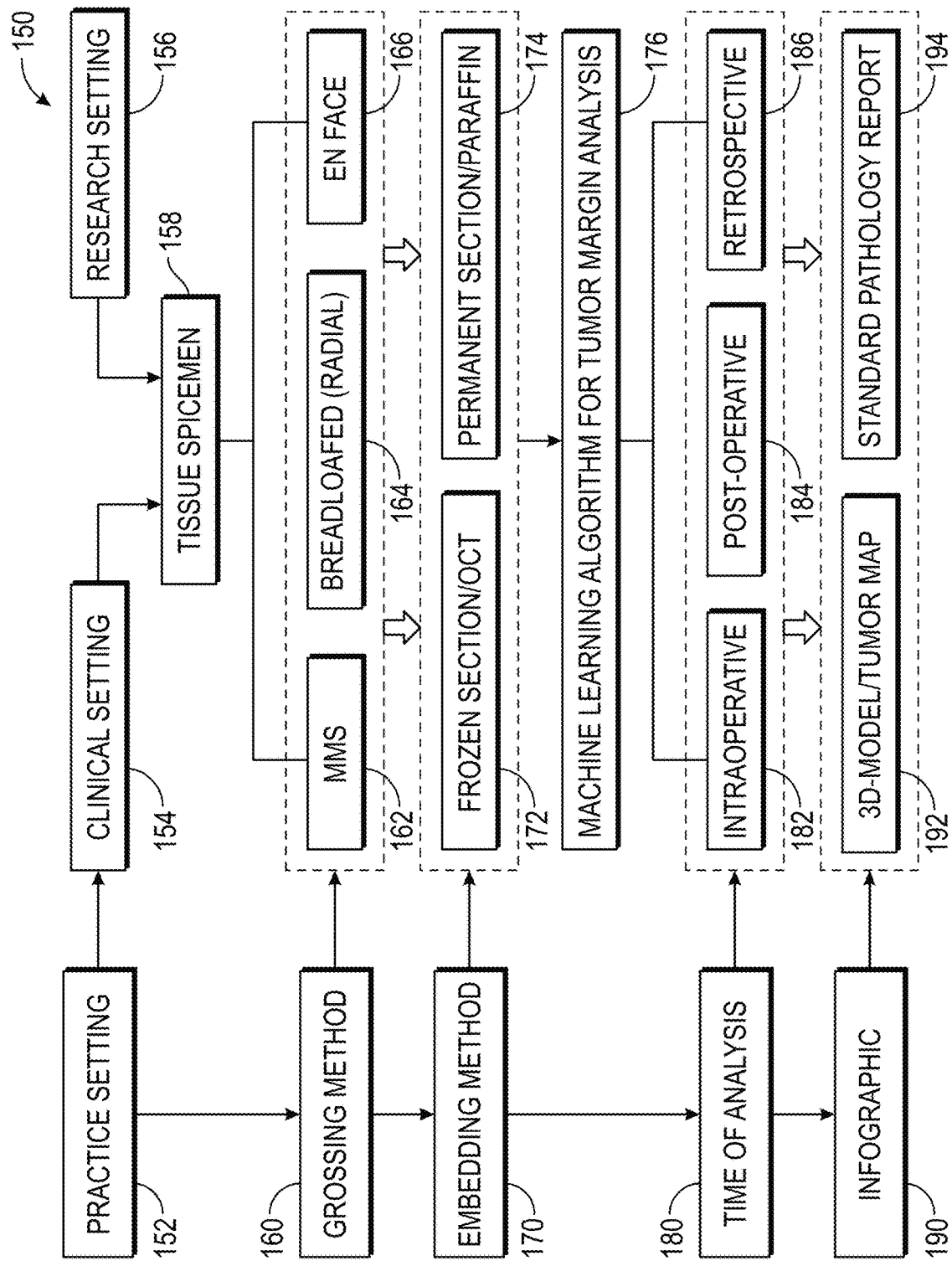
FIG. 1B is a diagram of the of the application of the system and method herein to both clinical and research settings, including but not limited to various tissue grossing techniques, embedding media and tissue processing approaches, timing of machine learning algorithm/process analysis, and output of an infographic and/or a report.

By way of further overview, FIG. 1B is a diagram 150 showing the settings 150, including a clinical setting 154 and a research setting 156 to which the machine learning algorithm/process described below can be employed/applied to analyze tissue specimen margins for the presence or absence of tumor. It shows that the algorithm/process can be applied to tissue 158 grossed in any form of grossing method/technique 160 including but not limited to MMS 162, En Face 164, Breadloafed sections (e.g. radial) 166 and embedded (170) in either OCT for frozen sections 172 or paraffin for permanent sections 174. The algorithm/process 176 can then be applied to these embedded specimens (170). More particularly, the algorithm/process 176 is applied at various times (180), that is, in real-time for intraoperative margin assessment 182 which would most commonly employ frozen sections, or in post-operative margin assessment 184, which would most commonly employ paraffin embedded sections. The algorithm/process 176 can also be applied in a retrospective analysis 186, after a procedure. As a result of the analysis 180 by the machine learning algorithm/process 176, infographics 190 of analysis results and associated information are generated. The infographics 190 can include 3D models and tumor maps 192 of the tissue and/or a standard pathology report 194, both of which can be generated automatically with the ability to be communicated/displayed and viewed in real-time, and also uploaded to a patient's electronic medical record.

II. Overview of Hardware and Software Arrangement

Figure 2:
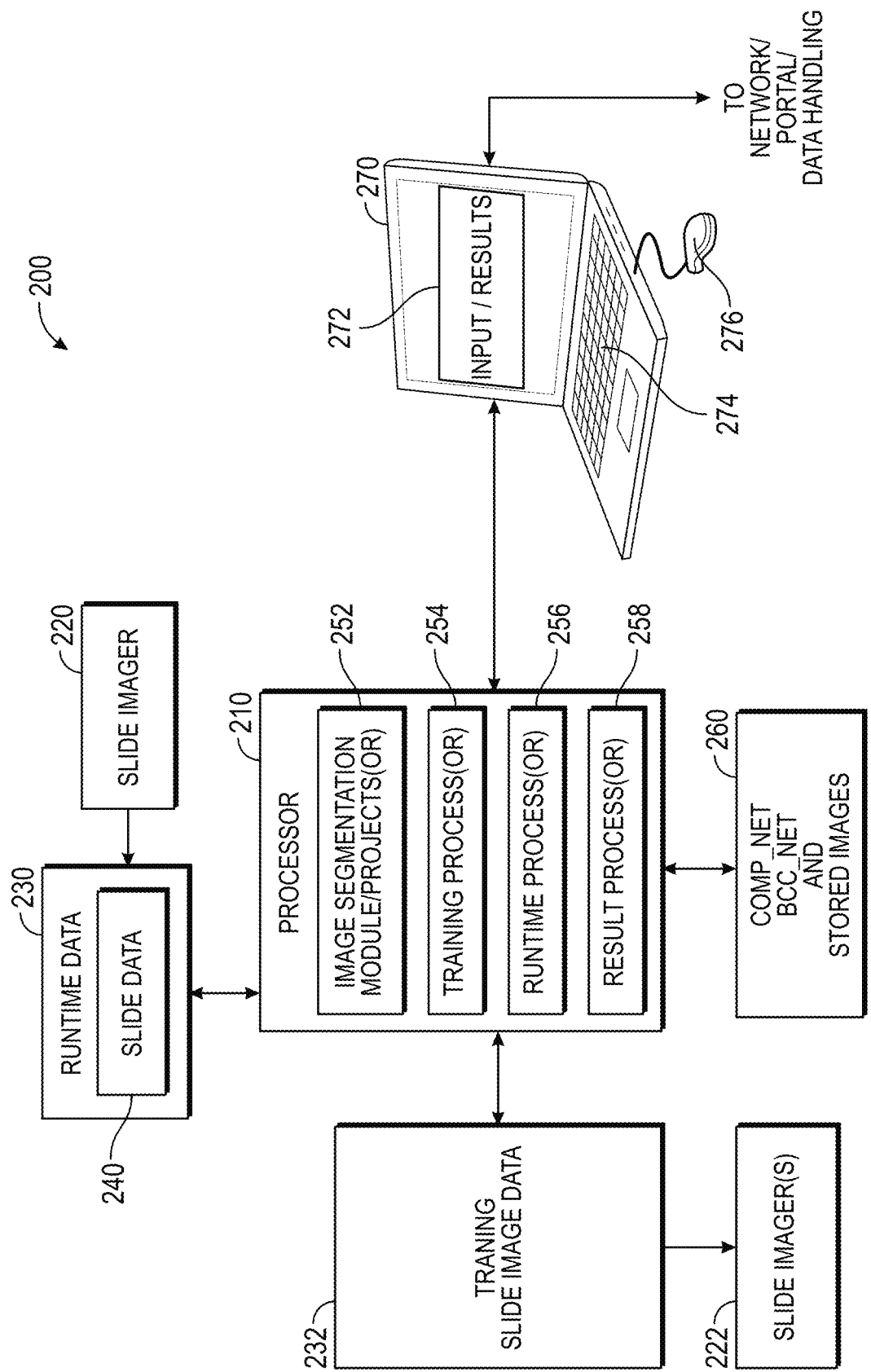
FIG. 2 is a schematic diagram of an overall hardware and software arrangement in which the illustrative system and method operates, according to an exemplary embodiment.

Having described an overview of an exemplary tissue specimen preparation technique and the settings, timing and results of the system and method herein, the following is a more-detailed description of the structure and function of the system and method. FIG. 2 shows an arrangement 200 for diagnosing conditions (e.g. various forms of cancer, including, but not limited to, melanoma, squamous cell carcinoma, basal cell carcinoma (BCC), breast cancer, colon cancer, brain cancer, etc.) based upon tissue sample slides prepared from patient tissue as part of a treatment diagnosis and regime or tissue sample slides prepared from animal models as part of a research study. The arrangement includes a computing processor 210 that can be any acceptable system, such as a server, laptop, PC, cloud computing environment, etc. The processor 210 receives image data from a variety of sources, including, but not limited to one or more slide imagers 220, 222 that transform optical information from a part of, or whole, slides, via a microscope optics and associated image sensor, into digital image data in a desired format. In a non-limiting example Leica Aperia AT2 slide scanner, operating at 20× optical magnification, can be used to create 40K×40K pixel whole slide images (WSI). Six to eight tissue sections can be imaged in an exemplary implementation.

As described further below, the slide imager 220 is used in the field to image patient slides for diagnosis in runtime, and this data 230 is thereby presented to the processor 210. One or more (other) slide imagers 222 can be part of a related or unrelated system that produces a large volume of slide image data based upon various types of cells and/or conditions. This data 232 is part of a training set that is input to the processor 210 for use in construction a machine learning (AI) network (i.e. COMP_NET and BCC_NET) as described further below. Such machine learning can be based upon a variety of architectures and associated computing algorithms/software×for example, a convolutional neural network CNN. Note that the processor 210 is generally representative of one or more processing/computing devices that can be used in any of the stages of the overall system and method. In practice, one processor can be used to train the CNN, while another processor produces final images and even another is used to operate a runtime portal accessed by practitioners seeking to analyze one or more patient slides using the system and method. Hence, the term "processor" or "computing device" as used herein should be taken broadly to include one or more discrete processors/computing devices used at one or more stages of the over training and/or runtime operation of the system and method. Note also that further description related to the scanning of tissue slides, and handling data thereof, can be found in U.S. patent application Ser. No. 16/679,133, entitled SYSTEM AND METHOD FOR ANALYZING CYTOLOGICAL TISSUE PREPARATIONS, filed Nov. 8, 2019 by Louis J. Vaickus, the teachings of which are incorporated by reference as useful background information.

The processor 210 contains a plurality of functional processes(ors) or modules. There is an image segmentation module/process(or) 252 that allows both training and runtime slides to be broken into smaller feature sets for reduction in processing overhead and/or to identify specific conditions within the data. This can allow for comparison, as well as masking and other image processing operations described below. A training module/process(or) 254 controls the construction of the machine learning network(s) 260, which is stored along with appropriate classifiers, image data, etc. as shown. Likewise, a runtime module/process(or) 256 controls application of the machine learning network 260 to runtime image data 230 to achieve diagnostic results. These results are handled by a result module/process(or) 258 that can present desired information graphically and/or textually as desired.

The process(or) 210 can be part of, or in communication with, a computing device 270, which as described below can be any acceptable computing device or group of computing devices. The computing device 270 can handle or manage system settings, user inputs and result outputs. The computing device 270 herein includes an exemplary graphical user interface (GUI) having a display (e.g. a touchscreen 272, mouse 274 and keyboard 276). The computing device 270 can interface with various network assets/data utilization devices, such as data storage, printers, display, robots, network ports, etc. Again, while the interface/display device (computing device 270) herein is shown as a standalone PC or laptop with separate keyboard and mouse, this can be representative of any acceptable platform for entering, receiving and manipulating information, including those with a single all-in-one functionality (e.g. a touchscreen display), such as found on a smartphone, tablet or miniaturized laptop.

It is recognized that machine learning has been used in multiple fields for histologic diagnosis, but to date, has not been used for margin analysis. The ability to rapidly analyze tissue margins and accurately map the tumor provides the ability to expand the use of en face/MMS type margins into all areas of tumor resection in real-time. This system also decreases the amount of time it takes a pathologist to read an increased number of breadloafed paraffin sections thereby allowing for an increase of margin analyzed while decreasing the amount of tissue required to read the tissue sections. In both instances machine learning provides the opportunity to decrease the possibility of the pathologist missing the presence of tumor at a margin and calling it a clear margin when in fact the tumor involves the tissue margin.

III. System Overview and Operation

Figure 3A:
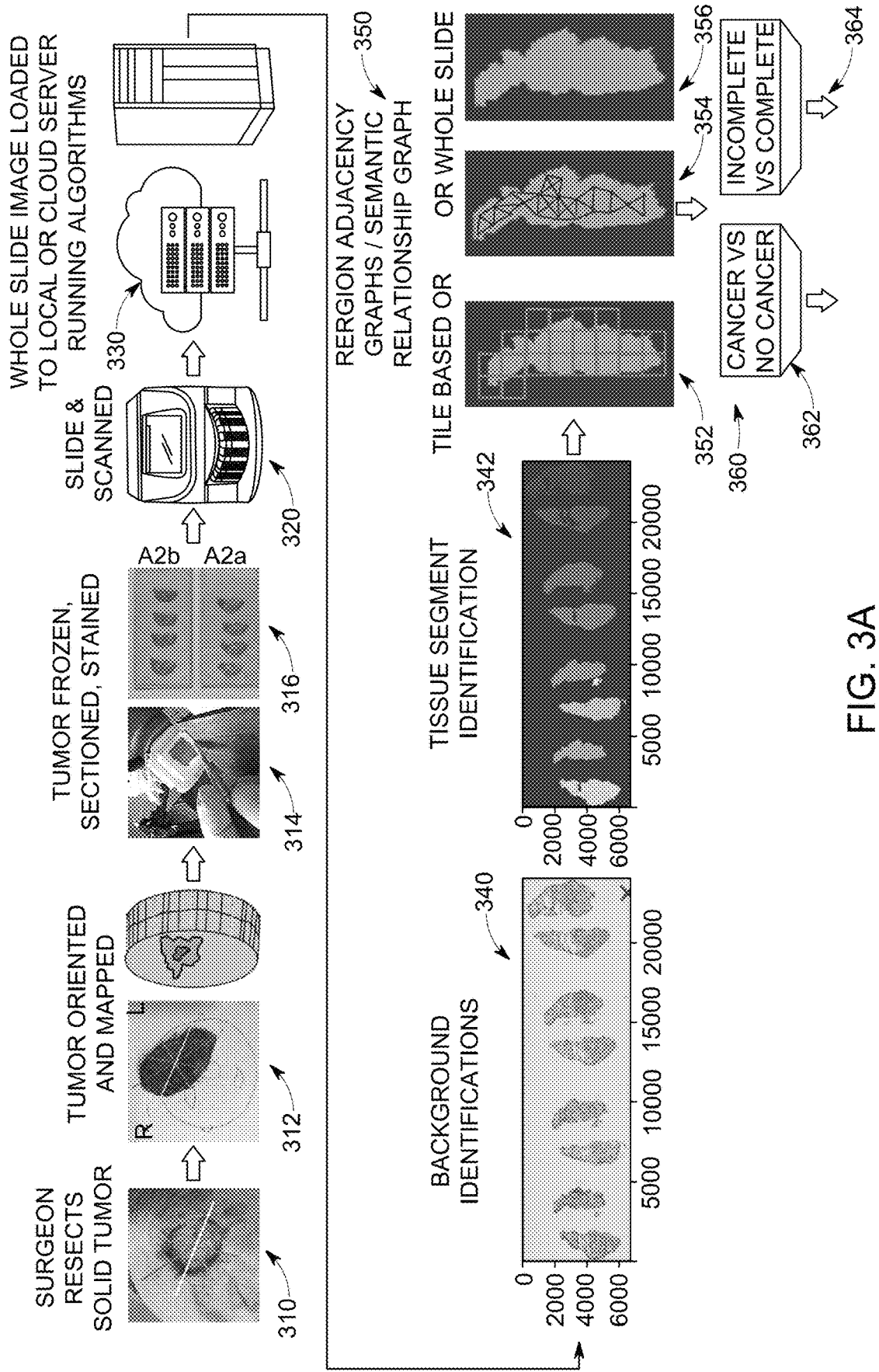
FIGS. 3A and 3B are two parts of an overall flow diagram showing the various procedure steps in an overall workflow of the system and method of FIG. 2.
Figure 3B:
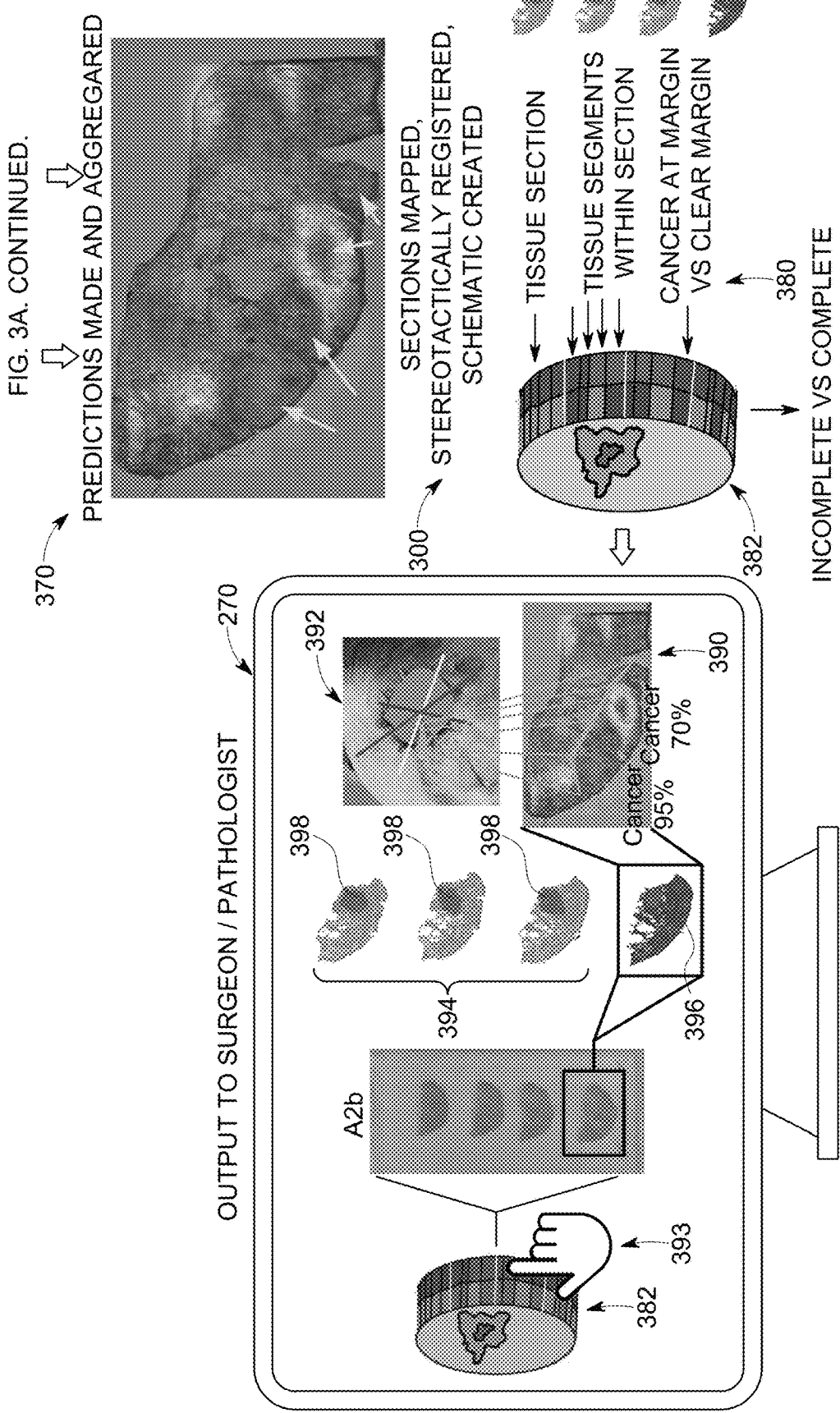

Reference is made to FIGS. 3A and 3B, which together graphically depict the overall flow of data and operational procedure steps 300 in association with both training and runtime operation of the system and method herein. As shown, the workflow begins with the excision or resection of a solid mass of tissue from a patient in step 310. Then, in step 312, the tumor within the tissue is oriented and mapped. Next, in step 314, the tissue is frozen, sectioned (e.g. by en face, MMS, breadloafed etc.) and stained (substep 316) using an appropriate staining method known to those of skill. Note, if performing paraffin embedded sections, step 314 would involve tissue processing, paraffin embedding, and, sectioning. Next, in step 320, a conventional or custom slide scanner acquires one or more image(s) of the stained slide(s). These images are converted to digital image data—typically color and/or grayscale—that can be stored and used for follow-on processing according to the system and method. In step 330, the image data (for example, whole slide data) can be transferred/downloaded to a local and/or cloud computing environment—for example, one or more server(s), that conduct image analysis on the slides based upon machine learning processes described further below. These processes entail plurality of steps that are described in further detail below. The steps include background identification 340 and tissue segment identification 342. Data/results 350, including tile based images 352, region-adjacency or semantic relationship graphs 354 and/or whole slides are fed to computing processes 360 that determine cancer versus no cancer (BCC_NET) 362 and/or complete versus incomplete tissue images (COMP_NET) 364. The outputs of such processes 360 are then used to create predictions of tumor presence, size and shape (image 370). The predictions are used to generate a model 380. This process, described further below, entails mapping the sections of the tissue from the slides, stereotactically registering the sections, and then creating a schematic 382 that can be part of an overall infographic representation (described further below). As shown, the results can be displayed to a practitioner or other interested party with associated annotations and highlights via the display 270. In this case, the display 270 depicts the relative location of modeled tumorous tissue 390 versus the patient's anatomy 392. Results can also be displayed as a standard pathology report in cases that the algorithm is used in post-operative margin analysis including but not limited to paraffin embedded breadloafed sections.

Note that the illustrations herein are presented in grayscale. However, it is expressly contemplated that the various displays, heat maps, infographics, tissue region differentiations, etc. can be depicted/displayed in a variety of colors symbolizing various information and/or conditions. Likewise, various monochromatic shadings, fill patterns or other representation can be used instead of, or in combination with color representations to characterize the information displayed herein. The implementation and/or use of such color-based and/or shading-based representations on a display should be clear to those of skill in the art.

Figure 4:
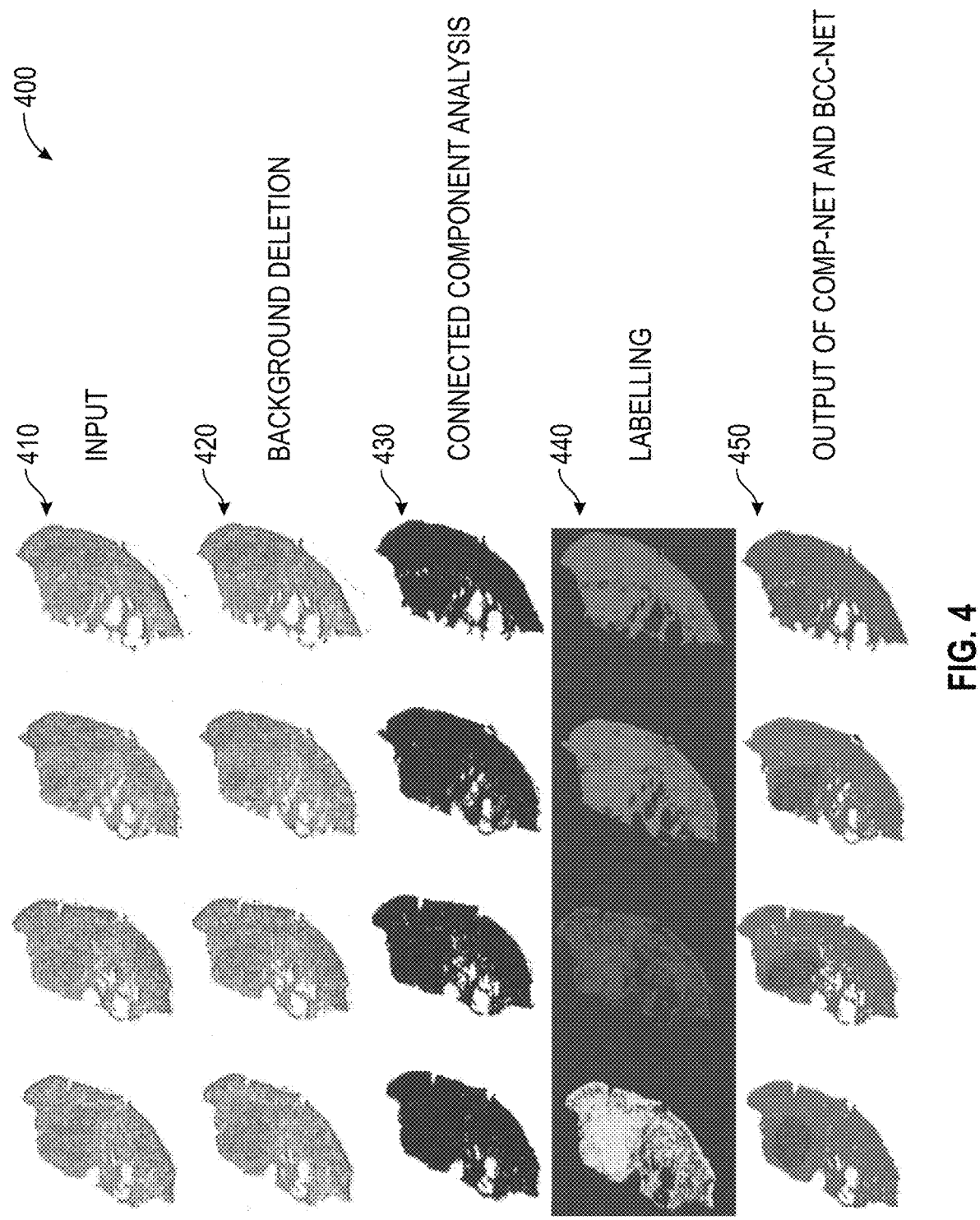
FIG. 4 is a plow diagram showing the processing of whole slide images (WSI) by the various processes of the system and method of FIG. 2.

Referring further to FIG. 4, the overall procedure 400 of processing images is shown. The procedure 400 entails inputting raw slide images in step 410, followed by background deletion in step 420. This can be accomplished using conventional or custom vision system tools, such as those that analyze blob, edges and/or contrast. The images are then subjected to connected component analysis (or a similar tool) to develop a continuous representation of the region (which can be expressed as a binary image) in step 430. The images are then subjected to a labelling process in step 440. Finally, the trained COMP_NET and BCC_NET processes operate on the images to generate results 450.

Figure 5:
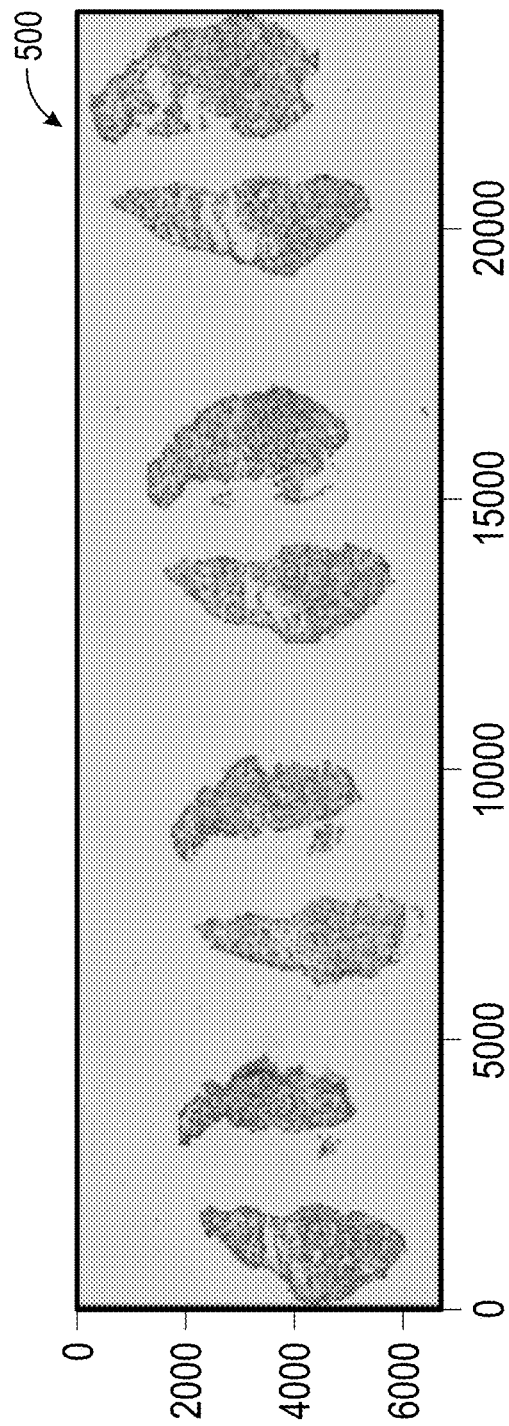
FIGS. 5 and 6 are images of slides associated with a complete versus incomplete analysis using the COMP_NET machine learning process according to the system and method of FIG. 2.
Figure 6:
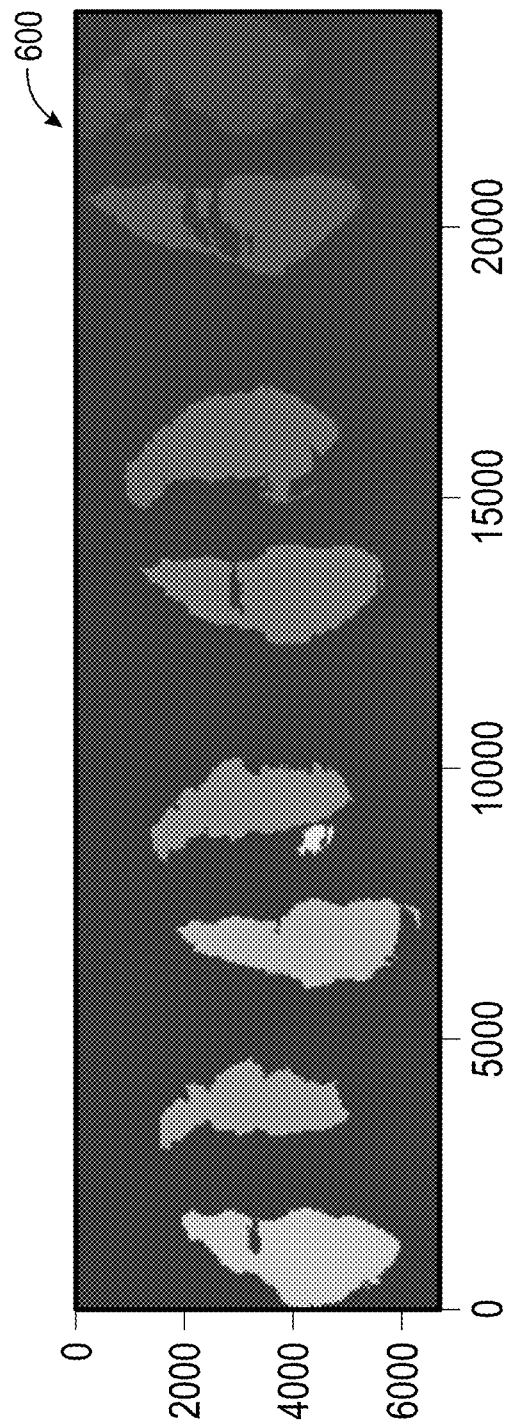

With reference now to FIGS. 5 and 6, the analysis of complete versus incomplete images by COMP_NET is described in further detail. Whole slide images (WSI) are extracted and converted to NPY file format 500. Background deletion then occurs via (e.g.) Otsu thresholding. Connected components (objects separated by background) are then identified and filtered by size. Each component is then evaluated by COMP_NET and given a "completeness" score. High risk components transmitted to surgeon and/or pathologist for evaluation from the results 600.

Figure 7:
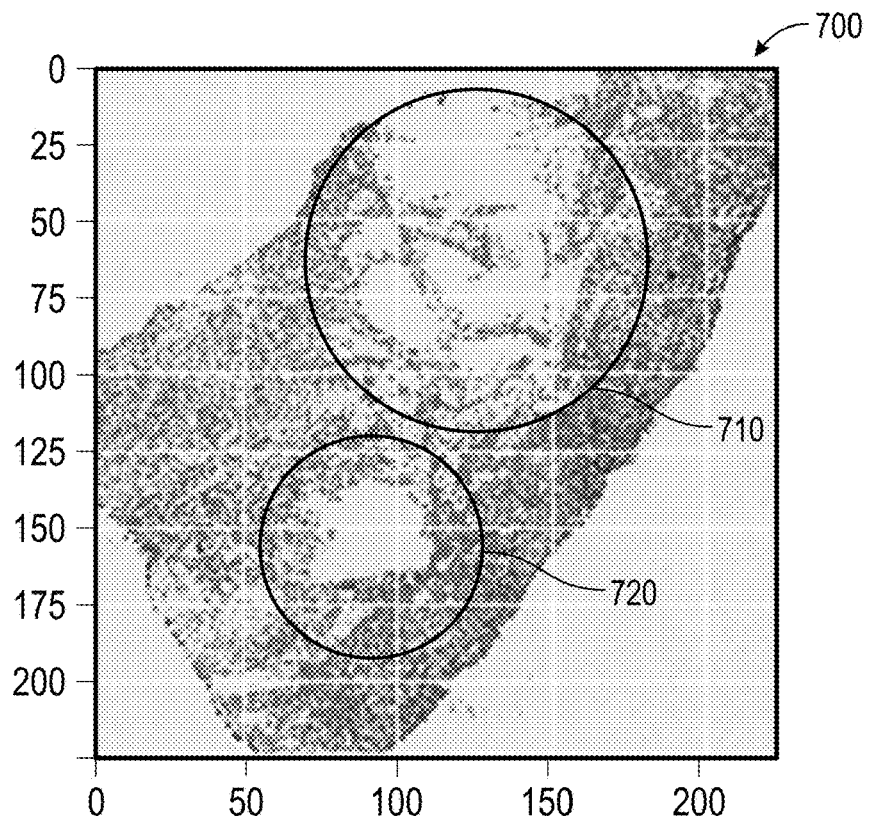
FIGS. 7 and 8 are images of slides associated with a positive or negative (e.g.) basal cell carcinoma (BCC) analysis using the BCC_NET machine learning process according to the system and method of FIG. 2.
Figure 8:
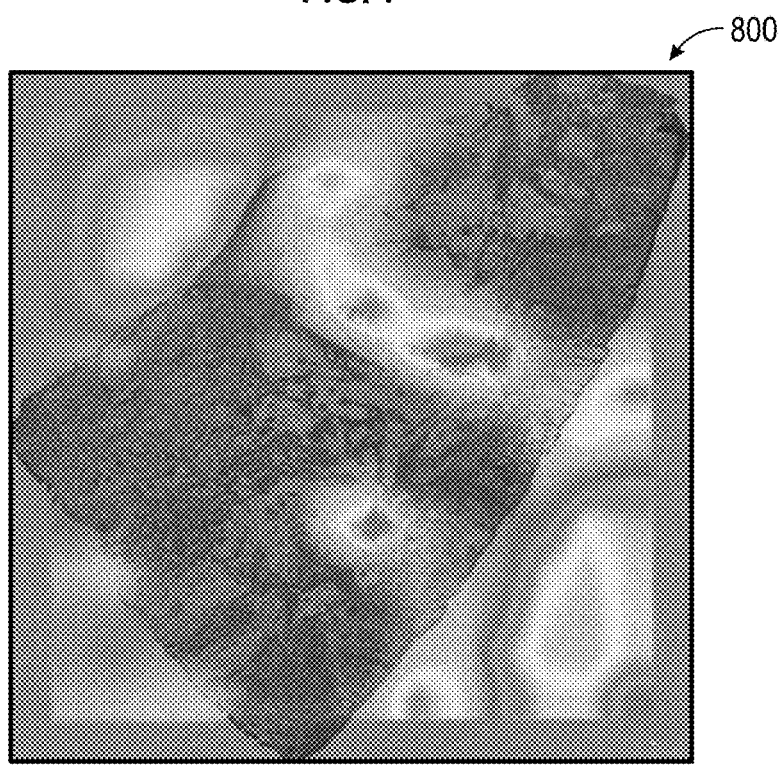
Figure 9:
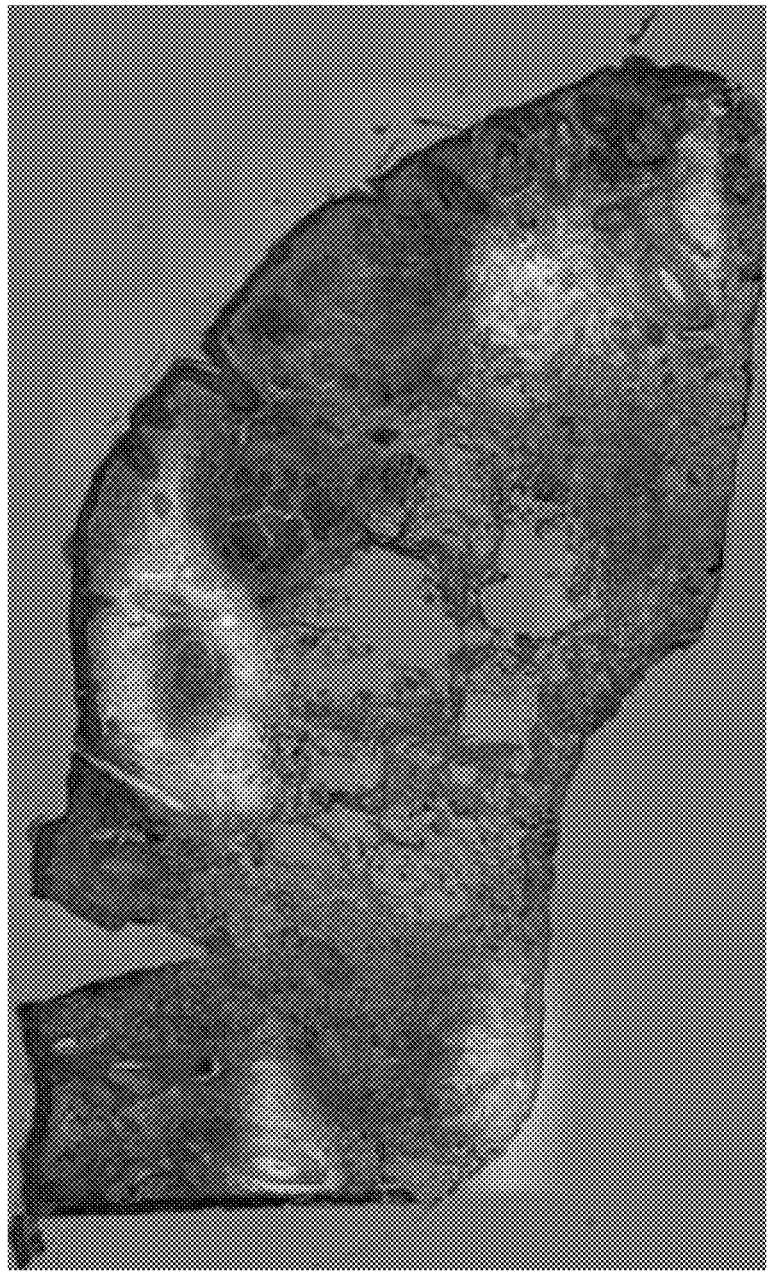
FIG. 9 is an image of a heat map of a tissue sample constructed based upon the results of COMP_NET and BCC_NET according to the system and method of FIG. 2.

The analysis of cancer presence versus absence in tissue images by BCC_NET is now described in further detail. With reference to FIG. 7, in the depicted exemplary image 700, the tumor (or high risk) regions 710 and 720 are indicated. The areas are further highlighted in the image 800 of FIG. 8. In operation, the initial model is trained. WSI are extracted and converted to NPY file format. Background deletion via (e.g.) Otsu thresholding then occurs. Connected components (objects separated by background) are identified and filtered by size. Each component is evaluated by BCC_NET and given a "carcinoma" score. High risk components transmitted to surgeon and/or pathologist for evaluation as part of the results 900 (FIG. 9).

The outputs from COMP_NET and BCC_NET are then applied to individual components. The components are registered with MixMatch (a Custom GPU accelerated gigapixel registration algorithm). The use of alternate registration procedures should be clear to those of skill. A 3D stereotactic infographic is then created and transmitted to surgeon. As shown in the display 270 of FIG. 3B, clicking (for example, touching with a cursor 393 different segments in different symbolic colors, shades and/or fill patterns) on infographic 382, using an appropriate interface device, brings up analyzed, highlighted WSI for that component for manual checking by the practitioner. The display 270 of FIG. 3B can also feed (e.g., using appropriate communication/network and interface/API arrangements) into a computer generated automated pathology report with both text and infographic display of the presence or absence of tumor at the specimen margin.

Figure 10:
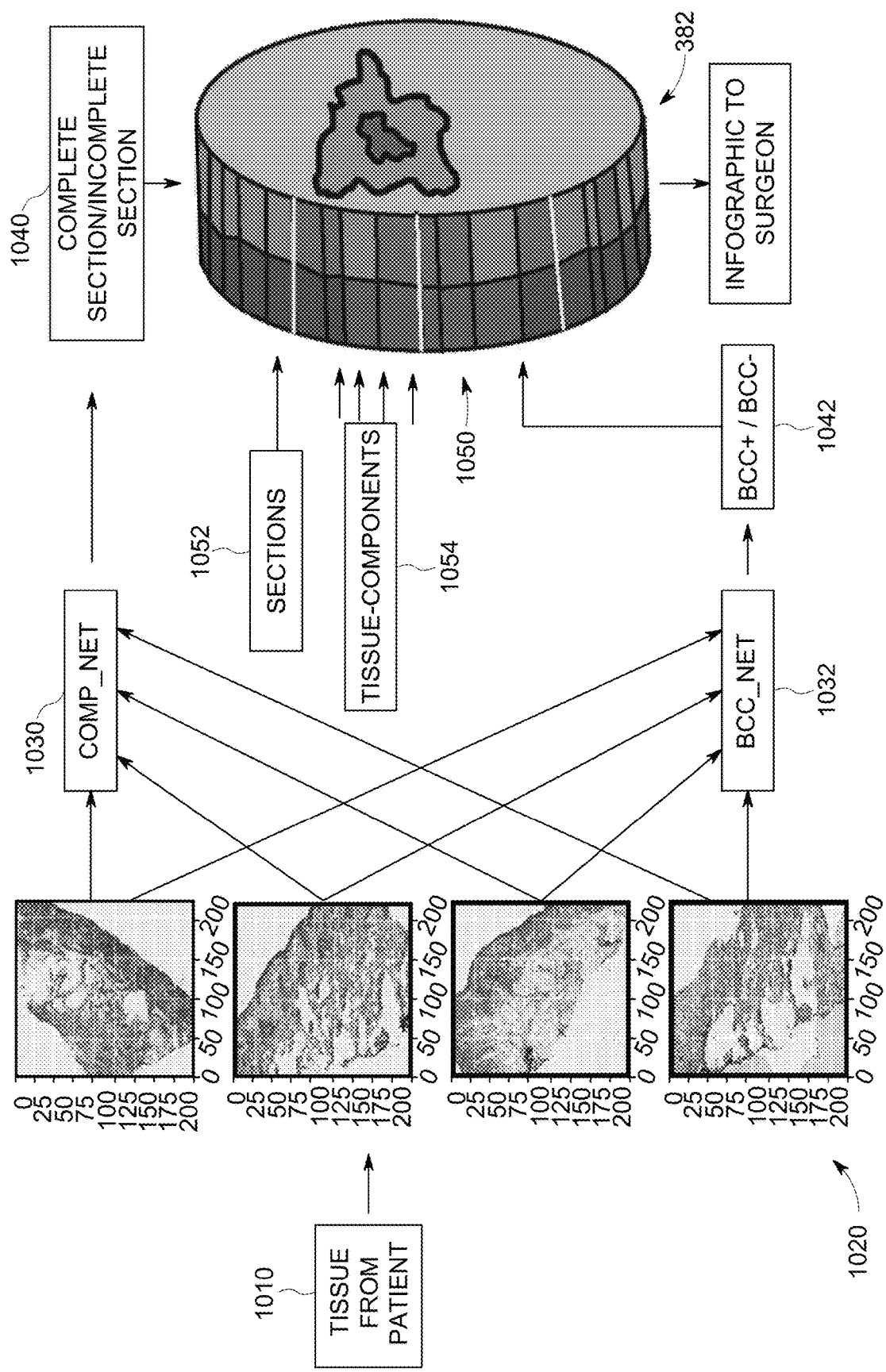
FIG. 10 is a schematic diagram showing the runtime model for generating and displaying an infographic for use by a practitioner (pathologist, surgeon, etc.) from tissue resected/excised from a patient according to the system and method of FIG. 2.

FIG. 10 further illustrates the overall operation of the system and method to create the color and/or shaded infographic 382 with interactive regions that can be clicked upon to reveal further information to the user. As shown, tissue 1010 from the patient or research specimen is provided in the form of whole slides that are prepared from the tissue via margin excision, freezing or paraffin embedding, slicing and staining. This allows for use of WSI to provide images 1020. These sections images have components identified using various computing processes and are fed to both COMP_NET 1030 and BCC_NET 1032. These algorithms/processes respectively produce complete/incomplete section results 1040 and positive or negative BCC results 1042. The results are combined into an infographic 1050 that is divided by sections 1052, which each display various types of tissue components 1054. Again, the actual display can employ various symbolic (discrete) colors, which are represented in grayscale in this depiction. More generally, the contemplated use of discrete colors, patterns and/or shades in displays, some of which allow clicked accesses to enhanced relevant data, can be termed "graphical differentiation" herein.

IV. Implementation Details

According to an embodiment, the above-described WSI are subjected to a series of morphological and thresholding preprocessing algorithms followed by background deletion and connected components analysis. The above-described, connected components analysis identifies and labels each of the individual pieces of tissue present on the WSI. Typically, each individual component represents a single histological section (unless a section becomes fragmented, which rarely occurs). The subimages from each WSI are grouped according to a pathologist assigned category (complete or incomplete section and by presence or absence of carcinoma, e.g., BCC). The subimages are then downsampled by a factor of (e.g.) 10 using bicubic interpolation, separated in to Train, Validation and Test sets and used to train a neural network (many architectures will be investigated). Model fit is evaluated by visual cluster analysis of latent feature vectors as well as by raw accuracy versus the validation set. The model hyperparameters are tuned until adequate performance is achieved (e.g., >95%) versus the validation set. The models final accuracy is then calculated versus a test set. Two models can be trained via this methods, with one network to evaluate a tissue section for completeness (COMP_NET) and one for evaluating for the presence of malignant tissue, in this case BCC (BCC_NET). Note that BCC_NET, instead of being trained on entire downsampled sections can be trained on 224×224 image subtiles from each section. The finished BCC_NET can operate by passing a sliding window receptive field over an input image with a high degree of overlap and summing BCC scores per area to create a heat map (see FIGS. 8 and 9, and 370, 390 in FIG. 3B) of potential BCC locations.

Once these models are trained they are then added to a hybrid algorithm, which performs the following functions for all incoming images: (a) scanning, (b) preprocessing, (b) completeness evaluation (c) malignancy evaluation, (d) outputting information to the surgeon.

In operation, following slide cutting and staining, a local scanning device produces (e.g.) 20× scans as rapidly as possible (note that current Leica scanners (described above) can produce a 40× scan in 40 seconds). Following scanning, the image can be saved to a "To Process" folder on an adjacent computing workstation. A process can be assigned to the incoming image, and the WSI will be loaded into RAM as a (e.g.) Numpy array for processing. The image is also normalized, deleting the background and performing connected component analysis to identify tissue sections. Each section can then be downsampled. The downsampled images are accepted, and using COMP_NET, a binary prediction COMPLETE or INCOMPLETE is produced. AIM4 will pass the same subimages on to BCC_NET to render a binary prediction BCC or NEGATIVE. The evaluation can be transmitted to a display device (monitor 270 in FIGS. 2 and 3B) in the operating room, which displays a representation of the resected tissue organized by location in the operative site. Alternatively, if not being performed in real-time the evaluation can be used to generate an automated pathology report to be transmitted to the practitioner. If all sections are complete for a margin, a series of overall (e.g.) green-shaded images (394 in FIG. 3B) can appear indicating the number of tissue sections analyzed representing the shape of the tissue segment analyzed (so the histotechnologist and surgeon can check for erroneous breaks in the tissue). In the event of incomplete margins the sections which were deemed incomplete can be displayed/represented in a contrasting color or graphic, such as red (396). Each segment can also be subtended with a BCC+ or BCC− title and/or areas of supposed BCC will be highlighted/represented in another contrasting color or graphic, such as purple (398). More generally, it can be seen how the cursor 393 causes selection of a set of slides with emphasis on a selected color/condition in slide 396 that is associated to that region. This is enlarged to a more detailed view in the (heat-map-based) tissue image 390. This image is, itself, linked to the displayed photo of the patient's anatomy 392—in this exemplary case, a region of the head in which a skin section has been excised, leaving an outline of skin surrounding the underlying exposed tissue.

In various embodiments, preprocessing can also include further steps of registration and 3D reconstruction. Following connected component analysis, the image of each section is provided with an order, (e.g. 1, 2, 3, 4, 5, etc.) based upon the order in which the histotechnologist cut the sections (which is typically the same every time). Briefly, the second section can be registered with the first section, the third section with the second section, and so on, until a table of registration coordinates has been created. This table can specify translation, rotation and warping operations in order to most precisely align each section with its preceding section. Knowing that each retained section is separated from its predecessor by a fixed number of 5 micron-thick sections, the system can then construct a 3D reconstruction of the original tissue. On the resulting displayed diagram of the 3D reconstruction, the system can then highlight where in 3D space any incomplete margins are located, and the location of BCC.

V. Services and Equipment

The above-described system and method can be offered to practitioners and facilities as an independent, (e.g.) subscription or per-use-fee-based service where each laboratory wanting to use the technology purchases or leases an appropriate whole slide scanner, a local workstation (which will run the proprietary software used by the system and method) and a display for the operating room, which is linked to the workstation. Arrangements can be made whereby such laboratories provide additional training data from their runtime operations to improve the training data/machine learning algorithms operated by the system and method. Any subscription or use-based service can include appropriate secure Internet (or other network-based) communications protocol layers and associated secure financial transaction processes. Appropriate passwords can be employed by users to authenticate access in a manner clear to those of skill.

In a client-service environment the following can be offered by the operator of the system and method (in whole or part):

A. Intraoperative Margin Assessment (IMA)

IMA can provide 3D AI assessment of sectionings including but not limited to, MMS, en face breadloaf (radial) margins in real time to surgeons during operations via an intuitive infographic.

Requirements for Client:
1. Dedicated whole slide scanner, which can be purchased by the customer or leased from the service.
2. Either (1) Internet upload speed of at least (e.g.) 25 Mbs or (2) dedicated server purchased from service, preloaded with licensed software. This device can be redundant, e.g. a double server.
3. If the client has insufficient bandwidth for real time uploads OR does not wish to purchase a server, their images will be uploaded to our cloud service which can be strategically deployed to servers physically near the client's location.
4. For the IMA cloud service, WSI can be uploaded to the service's cloud servers and processed in the fastest possible tier: STAT (can employ a very fast cloud computing instance). This service can also be utilized for server customers if their local hardware fails.

B. Post-Operative Margin Assessment (POMA)

POMA can provide 3D AI assessment of tissue margins including but not limited to MMS, en face or breadloaf (radial) frozen sections or paraffin embedded sections of surgical cases or research studies for the purposes of increasing the number of tissue sections analyzed, decreasing time for pathologist to read slides, and increasing accuracy of pathologist read.

Requirements for Client: As Above for IMA

C. Retrospective Margin Assessment (RMA)

RMA can provide 3D AI assessment of tissue margins including but not limited to MMS, en face or breadloaf (radial) frozen sections or paraffin embedded sections of surgical cases or research studies for the purposes of training, education and (e.g.) legal/administrative cases.

Requirements for Client:
1. Access to physical slides or whole slide images (WSI).
2. Physical slides can be shipped to service's physical location and scanned and uploaded to our cloud service at the customer specified tier.
3. For the RMA cloud service, WSI can be uploaded to service's cloud servers and processed in different services tiers, depending on how fast the client wants results: STAT (can employ a very fast cloud computing instance), EXPEDITE (can employ a slower instance), ROUTINE (can employ the base GPU instance), SLOW (will utilize spot instances), PRO BONO (can process during downtime, on certain paid instances or in special circumstances).
4. The client can receive back assessments of each margin and 3D infographics as it would have appeared during a live operation.

C. Aggressiveness Risk Assessment (ARA):

ARA can analyze cases retrospectively for IMA, POMA and RMA customers and provide a risk assessment for both local recurrence (LR) and metastasis (M).

Requirements for Client:
1. Be part of either or ARA or RMA program.
2. Client can select either LR, M or LR/M (combo with (e.g.) favorable price reduction).
3. Results can be computed either locally, or in the cloud (cloud speed tier rates apply).
4. Results for LR and M can be provided as: Low Risk, Moderate Risk, High Risk, or Indeterminate (for example, fees/charged for Indeterminate can be waived).

VI. Conclusion

It should be clear that the above-described system and method provides a highly robust and desirable tool for diagnosing and analyzing tissue for the effectiveness of a treatment in the context of tumor resection. This system and method operates with all common forms of histology and provides a rapid, accurate, user-friendly, repeatable, and continually improving result to practitioners and researchers.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A method for generating, with a processor, a model of tissue for use in diagnostic and surgical clinical and research procedures comprising the steps of:
receiving whole slide images (WSI) of tissue removed from a patient or a research specimen;
determining, using a machine learning process operating on the processor and trained on a set of tissue type-separated images,
(a) if each image of the WSI is of a tissue type that contains complete or incomplete tissue samples, based on a sample completeness score thereof, and (b) if each of a plurality of segments of the image of the WSI is of a tissue type that contains tumorous tissue or an absence of tumorous tissue based on a margin analysis thereof;

generating, with the processor, a visual model of the removed tissue based on a plurality of the WSI containing complete tissue samples prepared in a sequence, the visual model mapping of types tissue segments determined by the machine learning process across adjacent WSI in the prepared sequence; and facilitating use and manipulation of the visual model by a user in an interactive interface via a display under control of the processor, or use in a pathology report.

2. The method as set forth in claim 1, further comprising, training the machine learning process using a plurality of training slide images having a plurality of differing tissue types and arrangements.

3. The method as set forth in claim 1, further comprising, pre-processing each of the slide images prior to the step of determining, using the machine learning process, by performing a background removal process and a connected component process.

4. The method as set forth in claim 1, wherein the model defines differing sections of the tissue based upon each of the slide images and components of the tissue within each of the sections.

5. The method as set forth in claim 4, wherein the step of providing includes displaying an infographic that is arranged to allow the user to access further information or images with respect to the sections or the components of the tissue via a user interface.

6. The method as set forth in claim 5, further comprising, performing an access control process that authenticates the user relative to a remote server and performing a billing process that generates financial transactions between the user and an operator with respect to user operation of the method.

7. The method as set forth in claim 1, wherein slides associated with the WSI are prepared using frozen sections or paraffin embedded sections of the tissue, and the tissue is grossed using an MMS, en face or breadloaf (radial) technique.

8. The method as set forth in claim 2, further comprising, providing the training slide images via at least one of a library of preexisting images of tissue from third parties and preexisting images generated and stored by the user.

9. The method as set forth in claim 5, wherein the infographic includes a plurality of colors or other graphical representation that correspond to different types of tissue.

10. The method as set forth in claim 1, further comprising, operating the machine learning, at least in part, on a remote server accessed by the user via a network.

11. The method as set forth in claim 10, further comprising, performing at least one of (a) an access control process that authenticates the user relative to the remote server, and (b) a billing process that generates financial transactions between the user and an operator with respect to user operation of the method.

12. The method as set forth in claim 1, further comprising, operating a whole slide imager arranged to read each WSI prepared by the user and provide the slide images therefrom to the machine learning process.

13. The method as set forth in claim 1, further comprising, preparing the slides associated with the WSI using frozen sections or paraffin embedded sections of the tissue.

14. The method as set forth in claim 13, further comprising, grossing the tissue using an MMS, en face or breadloaf (radial) technique.

15. The method as set forth in claim 1, wherein the pathology report includes a readout that is adapted to be uploaded to a chart of the patient.

16. A system for generating a model of tissue for use in diagnostic and surgical and research procedures comprising:

a set of whole slide images (WSI) of tissue removed from a patient or a research specimen;

a machine learning system trained on a set of tissue type-separated images and determining for each image in the set of WSI:
  (a) a sample completeness score and based thereon if the image depicts a tissue type that contains a complete or an incomplete tissue sample, and
  (b) a margin analysis and based thereon if a plurality of segments of the image is of a tissue type that contains tumorous tissue or an absence of tumorous tissue; and a processor configured with computer executable code by which the processor:
  (a) generates a visual model of the removed tissue based on a plurality of the WSI containing complete tissue samples prepared in a sequence, the visual model mapping types of tissue segments determined by the machine learning system across adjacent WSI in the prepared sequence; and
  (b) facilitates use and manipulation of the visual model by a user in an interactive interface via a display under control of the processor, or use in a pathology report.

17. The system as set forth in claim 16, wherein the visual model defines differing sections of the tissue based upon each of the slide images and components of the tissue within each of the sections.

18. The system as set forth in claim 16, wherein the machine learning system operates, at least in part, on a remote server accessed via a network.

19. The system as set forth in claim 16, further comprising a whole slide imager arranged to read each WSI and provide the slide images therefrom to the machine learning system.

20. The system as set forth in claim 16, wherein the pathology report includes a readout that is adapted to be uploaded to a chart of the patient.

* * * * *